US006572593B1

(12) United States Patent
Daum

(10) Patent No.: US 6,572,593 B1
(45) Date of Patent: *Jun. 3, 2003

(54) DEFLECTABLE NEEDLE ASSEMBLY

(75) Inventor: Wolfgang Rudolf Daum, Neu Schlagdorf (DE)

(73) Assignee: Daum GmbH (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 731 days.

(21) Appl. No.: 08/552,143

(22) Filed: Nov. 2, 1995

(30) Foreign Application Priority Data

Nov. 13, 1994 (DE) .......................................... 44 40 346

(51) Int. Cl.[7] .............................................. A61M 25/00
(52) U.S. Cl. .............. 604/264; 604/164.13; 604/164.16
(58) Field of Search .......................... 128/772; 604/280, 604/281, 282, 19, 21, 27, 42, 506, 508, 164.11, 164.13, 170.02, 164.06, 170.03, 264, 272

(56) References Cited

U.S. PATENT DOCUMENTS

| 4,230,123 A | * | 10/1980 | Hawkins, Jr. ............ 128/772 X |
| 4,307,723 A | * | 12/1981 | Finney .................... 604/281 X |
| 4,573,470 A | * | 3/1986 | Samson et al. ......... 128/772 X |
| 4,643,194 A | * | 2/1987 | Fogarty .................. 128/772 X |
| 4,659,328 A | * | 4/1987 | Potter et al. ............ 128/772 X |
| 4,665,906 A | | 5/1987 | Jervis |
| 4,671,795 A | * | 6/1987 | Mulchin ..................... 604/281 |
| 4,688,554 A | * | 8/1987 | Habib .................... 604/282 X |
| 4,874,360 A | * | 10/1989 | Goldberg et al. ....... 604/281 X |
| 4,886,067 A | * | 12/1989 | Palermo ................. 128/772 X |
| 5,066,285 A | * | 11/1991 | Hillstead ................ 128/772 X |
| 5,597,378 A | * | 1/1997 | Jervis ..................... 604/281 X |

FOREIGN PATENT DOCUMENTS

DE          42 23 897 A1      1/1994

OTHER PUBLICATIONS

Copy of Product Literature "Smart Guide" publicly available Jun. 13, 1995.

* cited by examiner

Primary Examiner—Sam Rimell
(74) Attorney, Agent, or Firm—Saliwanchik, Lloyd & Saliwanchik

(57) ABSTRACT

The present invention provides a deflectable needle system for use in performing diagnostic or therapeutic medical procedures. The needle assembly of the invention provides access to physiological sites which may be inaccessible by prior art needle systems due to an obstruction. The deflectable needle assembly includes a telescoping cannula, catheter and stylet. The catheter component of the assembly is curved at its distal end and axially rotatable within the lumen of the cannula providing simple maneuverability for accurate placement of the catheter at a chosen physiological site.

16 Claims, 4 Drawing Sheets

DEFLECTABLE NEEDLE ASSEMBLY

FIELD OF THE INVENTION

The field of the present invention is a device for facilitating medical or surgical treatment in humans and animals. Specifically, the present invention provides a deflectable needle system for guiding a fluid or medical instrument to or from a location within the body and a method of use.

BACKGROUND OF THE INVENTION

The use of needles in the performance of diagnostic and therapeutic medical procedures is well known in the art. Needles come in various diameters and lengths to provide for parenteral administration of pharmaceutical or physiological therapeutic agents. Needles also provide access to anatomical regions of humans and animals for removal of blood, lymph, synovial fluid, cerebral spinal fluid, pericardial effusions, pleural effusions, vitreous fluid, and similar physiological fluids. Access to most anatomical regions provides a means for specific and enhanced diagnostic and therapeutic efficacy.

However, access to some anatomical regions using present needles is often difficult for the practitioner, or even dangerous to the patient, due to the obscure location of the region. Aside from the possibility of inaccessibility due to anatomic obstructions, along with access to some anatomical regions, using present needle systems, there is the possibility for iatrogenic trauma to the patient due to patient positioning, or due to puncture of a nearby organ during placement of the needle.

Accordingly, there is a need for a needle system which provides access to anatomical sites which are difficult to reach using present needle systems. There is also a need for the system to provide simple and accurate maneuverability during placement of the needle.

SUMMARY OF THE INVENTION

The present invention is a needle system which provides access to anatomical sites which may be difficult to access due to obstruction by a penetrable or non-penetrable barrier. The invention can be used to simply and accurately guide a needle to a desired physiological site.

The needle of the present invention is a deflectable needle assembly. The deflectable needle assembly provides for delivering or removing a material at a physiological site, in a human or animal body, when access to the site is obstructed by a an obstruction. According to the invention, a non-penetrable obstruction includes a parenchymal organ or other physiological tissue which could be pathologically damaged if penetrated by a needle. The deflectable needle assembly of the invention is a telescoping assembly including a stylet which inserts within the lumen of a catheter which inserts within the lumen of a cannula. All components are preferably rotatable around their axes.

The deflectable needle assembly as well as the individual component cannula, catheter, and stylet each have a proximal and distal end. The key aspect of the invention is that the distal end of the catheter is curved. The catheter is manufactured from a material which holds a curved shape and when forcibly straightened can return to its curved shape. Such materials for manufacture include elastic and superelastic compounds, for example, nickel titanium (NiTi). In addition, the components of the deflectable needle system may be manufactured from a material which may or may not cause artifact on images created by MRI, x-ray, and ultrasonic images.

The proximal end of the needle assembly as well as each of the components may also include a handle. A handle of the invention provides for holding or manipulation of the deflectable needle system during use. A handle on the catheter or cannula may include an egress or ingress channel for dispensing or removing fluid through the needle assembly.

The proximal handle of the deflectable needle assembly may also include a mechanism to prevent the catheter from sliding proximally or distally within the lumen of the cannula. The proximal handle assembly may also include a mechanism to inhibit fluid leakage at the proximal end of the deflectable needle assembly. In a preferred embodiment, a single unit performs both functions.

DETAILED DESCRIPTION OF THE INVENTION

Figure 1:
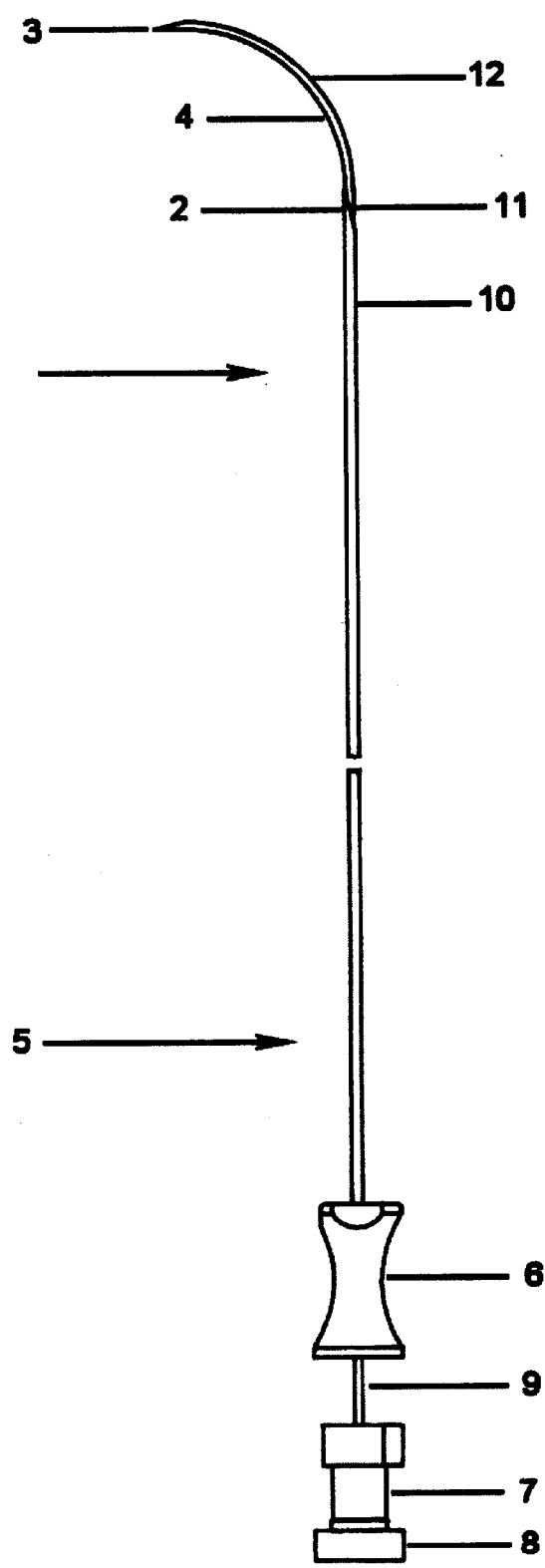
FIG. 1 is a view of one embodiment of a deflectable needle assembly of the invention.

The present invention provides a deflectable needle assembly for delivering or removing a fluid or guiding an instrument to a physiological site in a human or animal body. The invention claims priority to German Patent Application P 44 40 346.1 which is incorporated herein by reference.

It will be noted that in several places throughout the specification, guidance is provided through lists of examples. In each instance, the recited list serves only as a representative group. It is not meant, however, that the list is exclusive.

A needle assembly of the invention is a tubular, telescoping assembly which can penetrate a penetrable physiological barrier and can be used to transport a fluid or guide a medical instrument to, or from, a physiological location beyond the barrier penetrated. As will be described below, the assembly of the invention can incorporate the telescoping technology disclosed in German Patent Application DE 42 23 897 A1 which is also incorporated herein by reference. Preferably, the needle assembly can penetrate a penetrable physiological barrier, such as skin, meninges, or blood vessel wall, and provide for delivery or removal of a medical fluid at a physiological location which may be obstructed by bone or some other substantially non-penetrable barrier.

As used herein, a "needle" is defined as a slender hollow device for parenterally introducing or removing material from a human or animal body. A material which may be introduced or removed through the needle includes any material which can freely move through the needle including, fluids such as liquids, gases and suspensions, small particle solids, or slender objects including a slender surgical instrument.

A "deflectable needle assembly" or "puncture needle" of the invention includes, at least, a cannula, a catheter and a stylet. A key aspect of the invention is the use of a deflectable catheter which has a curved distal end which can be forcibly straightened but will return to its curved shape upon removal of the force. Generally the cannula, catheter and stylet can be rotated around a long axis. The combination of a curved distal end and axial rotation provide for manipulation around a non-penetrable obstacle.

A deflectable needle assembly of the invention can be used to penetrate a penetrable physiological barrier. As used herein a penetrable physiological barrier means any human or animal tissue which is readily penetrated by a sharp object, such as a needle, and include for example, skin, muscle (smooth, striated and cardiac), fat, fascia, tendons, ligaments, joint capsules, meninges, bladder wall, and similar tissues.

As used herein, a "physiological site" of a human or animal body is the location where it is desired to introduce or remove a medical fluid or provide access for a surgical instrument. Examples of physiological sites include, vessel lumens (blood and lymph)) ureter lumen, epidural space, subdural space, subarachnoid space, pericardial cavity, pleural cavity, peritoneal cavity and similar physiological spaces or potential spaces.

In a preferred embodiment, a needle assembly of the invention provides for dispensing or removing a material at a physiological site which may be obstructed by a non-penetrable barrier. Non-penetrable physiological barriers or obstacles include, for example, bone, cartilage and other tissues which are typically not readily penetrable by, for example, a needle. However, included in "nonpenetrable" obstacles may be, for example, a parenchymal organ which, although penetrable by a needle, may be pathologically damaged if penetrated. Hence, the present invention is useful for gaining access to a physiological site obstructed by an organ without having to penetrate through the organ. In addition, it is recognized that a non-penetrable obstacle may be present in a body which is not "physiological", but nonetheless, may be manipulated around by a device of the invention. For example, orthopedic hardware (eg. plates, wires, screws), electrode leads, etc.

As used herein a fluid which may be transported using a needle assembly of the invention includes a "medical fluid". A medical fluid includes physiological or pharmacological fluids which may be dispensed through a needle when performing a medical procedure. Such fluids include, for example, blood, serum, plasma, cerebral spinal fluid (CSF), synovial fluid, therapeutic agents (eg. antibiotics, chemotherapy, or electrolyte solutions), analgesic agents, anesthetic agents, contrast agents for diagnostic imaging systems (eg. radiopaque x-ray dyes, nuclear dyes, etc.). Medical instruments which may be guided through a needle assembly of the invention include, for example, microforceps, electrocautery probes, microscalpels, biopsy punch, transparent fibers for laser ablation and other slender instruments.

Therefore, a deflectable needle assembly of the invention has many uses. For example, a needle assembly may be used to dispense a diagnostic imaging agent at a localized site in the epidural space, which may be inaccessible with a non-deflectable needle due to obstruction by a bony vertebrae. The assembly may also be used to remove a CSF sample from the subarachnoid space. Alternatively, a deflectable needle assembly of the invention may be used to guide an electrocautery probe to a location not reachable by a straight guide system due to obstruction by an articular ridge or supporting ligament of a joint.

A deflectable needle assembly of the invention includes at least three components: a cannula (rigid external tube), a catheter (elastic middle tube), and a stylet (guide mandrin). Generally, the assembly of the invention and the individual components are elongate cylindrical structures. The catheter and cannula component of the invention also have an axial lumen. While it is not required, unlike the cannula and catheter, typically a stylet of the invention does not have a lumen. In addition, preferably, the cannula has a sharp or beveled edge to penetrate a penetratable tissue. It is not required that a catheter or stylet have a sharp edge.

The lumen of the cannula and catheter are defined by a wall. The inside diameter of a cannula or catheter is generally equal to the diameter of the lumen. The outside diameter of a cannula or catheter is the sum of two times the thickness of the wall plus the inside diameter. Obviously, if the stylet does not have a lumen, it will only have an outside diameter dimension.

In general, the catheter assembly is configured and arranged in a telescoping manner. By this it is meant that the components of the assembly fit together like sections of a telescope. For example, the telescoping arrangement of the assembly includes a stylet fitting inside the lumen of a catheter which fits inside the lumen of a cannula. Hence, the inside diameter of a catheter must be large enough to permit passage of the stylet into the catheter lumen. Similarly, the inside diameter of a cannula must be large enough to permit passage of a catheter. As will be described below, in one embodiment, a needle assembly may include multiple catheters each telescoping within another. If multiple catheters are used, each added catheter will have an incremently increased diameter.

A deflectable needle assembly of the invention has a proximal and distal end. Typically, the "distal end" is away from the operator and the "proximal end" is nearest the operator. As used herein, "distal end" refers to that end of the catheter assembly which penetrates a penetrable physiological barrier. Generally, at the least, the "proximal end" of the assembly provides a handle attached to the cannula with which to hold or manipulate the assembly during insertion and placement of the distal end at a physiological site. The proximal end will be further discussed below.

The distal most aspect of the distal end of the assembly is referred to as the "distal tip." Preferably, the distal tip has a beveled sharp (shared) edge. As used herein, a sharp edge an edge which can penetrate a penetratable physiological barrier. Like the assembly, each component of the needle assembly also has a proximal and distal end and a distal tip.

In typical use, the cannula facilitates placement of the catheter. However, it is the distal tip of the catheter which is ultimately located at the physiological site where the fluid will be dispensed or removed or to where an instrument is guided.

Generally, the catheter and stylet are substantially the same length, both longer than the cannula. During penetration of the assembly through a penetrable barrier, the distal tip of the catheter and stylet are typically retracted proximally within the lumen of the cannula, such that the distal tips of all components are, at the least, flush, providing a single beveled edge for penetration. Once the cannula has penetrated through a penetrable barrier the assembly may travel into a human or animal body. If an obstacle is encountered, the catheter and stylet may then be protracted distally out of the cannula lumen by pushing the below described catheter and stylet handles distally. If a stopper mechanism is present (described below) the stopper is removed or released to allow the catheter and stylet to be easily protracted distally. Moving the handles of the catheter and stylet distally provides for the catheter to "curve" around the obstruction. Rotation of one or both of the cannula or catheter around their axes provide further maneuverability to place the distal tip of the catheter at a selected site. The radius of the curve of the catheter may be selected based on the obstacle which will be encountered during a particular procedure.

Preferably, the stylet is maintained within the lumen of the catheter during insertion of the assembly. Once the catheter is at the desired location the stylet may be removed. The stylet provides stability to the catheter as well as prevents blockage of the lumen of the catheter during placement.

As can be seen, a key aspect of the present invention is that the distal end of the catheter is curved. As will be discussed below, the catheter is preferably made from a material capable of maintaining a curved shape and capable of returning to a pre-existing curved shape after being forcibly straightened by, for example, insertion of the catheter into the lumen of a cannula. The ability of the catheter to deflect from straight to curve, as well as rotate around its axis, allows the needle assembly to be manipulated around an obstruction. The radius of the curve of the catheter can be 0° to 180°, preferably 0° to 100° degrees.

In one embodiment of the invention, the needle system may include more than one catheter. According to this embodiment, each catheter telescopes within a larger catheter, all catheters being telescoped within a cannula. A telescoping system which may be used according to the invention is described in German Patent Application DE 42 23 897 A1 which is incorporated herein by reference. The use of multiple catheters which may each be rotated around their axes further provides access to physiological locations not available using only a straight needle.

The inside and outside diameter of the individual components of the assembly may vary. The overall outside diameter of the assembly is limited only by size constraints of the physiological site or any size constraints in the path the assembly takes in getting the distal tip of the catheter to the physiological site. The inside diameter of the catheter may vary depending on type of fluid or size of instrument which may be passed through the lumen. Preferred ranges of the inside diameter of the catheter for dispensing fluids is 0.1 mm to 15 mm, preferably 0.5 mm to 1.5 mm. Preferred maximum ranges for passage of instruments inside a needle is 2 mm to 15 mm preferably 2 mm to 5 mm. Preferred maximum range of the outside diameter of a cannula is generally 0.3 mm to 17 mm, preferably, 1 mm to 10 mm.

According to the invention, typically the cannula has a sharp distal tip for penetrating tissue. The cannula may be straight or curved but, unlike the catheter, the cannula typically is not deflectable. A cannula may be manufactured from any rigid metallic material known in the art including stainless steel. Alternatively, a cannula may be manufactured from alloys, including alloys of titanium, rigid plastics (e.g. polyetheretherketene, PEEK), ceramics, and other materials which are transparent on x-ray, MRI, or ultrasonographic images. On the other hand, cannulas may be manufactured to increase visualization under diagnostic imaging systems. For example, the outside surface of a cannula may be roughened to enhance visibility by ultrasound.

A catheter of the invention may be manufactured from any material capable of maintaining a curved shape and capable of returning to a pre-existing curved shape after being forcibly straightened by insertion of the catheter into the lumen of a cannula. Such materials include plastic, rubber, elastic, superelastic (pseudoelastic) alloys, and other materials having shape memory. Materials having shape memory or superelasticity, for example, nickel titanium (NiTi) are described, for example, in U.S. Pat. No. 4,665,906 which is incorporated herein by reference.

A stylet of the invention can be manufactured from any malleable material, for example, polyethylene and stainless steel wire.

A deflectable needle assembly of the invention also has a proximal end. Typically, the proximal end provides a mechanism for operating the deflectable needle assembly. Generally, at the least, the proximal end of the assembly may provide a handle from which to hold the assembly or manipulate the assembly during insertion and placement of the distal tip at a physiological site. In addition, the proximal end of the assembly may provide an egress\ingress channel for aspirating or dispensing fluid through the assembly. Preferably, the proximal end of the assembly also includes a mechanism for fixing the components of the assembly together as a unit. This provides, for example, for the distal tip of the catheter and stylet to be fixed within the lumen of the cannula during penetration of the assembly through a penetrable physiological barrier. The proximal end of an assembly may also provide a mechanism for inhibiting proximal leakage of fluid which is present at or around the distal end.

Generally, the proximal end of the assembly has a separate handle for each stylet, catheter, and cannula. In a typical figuration of the assembly, the handle of the cannula is located distal to the handle of the catheter. Hence, the handle of the cannula is configured and arranged with an orifice providing for passage of the catheter through the cannula handle.

Typically, the proximal end may also have an egress\ingress channel on each cannula or catheter handle for aspirating or dispensing fluid exclusively through either the cannula or the catheter. When the proximal end has both a handle and an egress\ingress channel, the handle and the channel may be a single molded unit. In one embodiment, two egress\ingress channels are present on the handle of a catheter. In this embodiment, one egress\ingress channel is configured and arranged for passing a stylet through the handle and into the lumen of the catheter. Preferably, the egress\ingress channel may be coupled, for example, to a fluid line or syringe using couplers known in the art, for example, luer locks, etc.

The proximal end of a deflectable needle assembly of the invention may also include a stopper which fixes the catheter in such a way as to prevent the catheter from sliding (telescoping) proximally or distally within the cannula. In addition to other functions, the stopper provides for atraumatic penetration by fixing the distal tips of the catheter and stylet within the lumen of the cannula, such that only the single sharp edge of the cannula contacts the penetrable barrier during penetration.

In one embodiment, the stopper may be a removable insert (distance part) which fits between the handle of the cannula and the handle of the catheter. Preferably, the length of the stopper is, at least, approximately equal to the length of catheter which extends beyond the distal tip of the cannula when the catheter is fully protracted distally. According to this embodiment, the stopper includes a lumen, through the length of the stopper, which is of sufficient diameter to fit around the outside diameter of the catheter. The stopper further includes a lateral slot along the length of the stopper which communicates with the lumen. The slot permits removal and installation of the stopper by passing the catheter laterally through the slot away from or towards the stopper lumen. In one preferred embodiment, the cannula handle, catheter handle, stylet handle and stopper may each have a geometrical attachment component (i.e., a projection or a projection receiving notch). Interconnection of a projection and a notch between each component handle provides for the deflectable needle assembly to be fixed as a single unit.

In an alternative embodiment, the stopper may be a structure which is slidably movable over the catheter and interposed between the proximal end of the cannula handle and the distal end of the catheter handle. According to this embodiment, the stopper has a peripheral and lumenal surface. The lumenal surface is in contact with the outside surface of the catheter. The stopper is of a material and configured and arranged such that compression of the stopper will cause compression of the lumenal surface around the catheter. Compression of the lumenal surface of the stopper around the catheter causes friction between the stopper and the catheter which fixes the catheter in such a way as to prevent the catheter from sliding proximally or distally within the lumen of the cannula.

In a preferred embodiment, the compressible stopper described above may be rigidly attached within a coupler having screw threads which can be threaded onto the proximal end of the handle of the cannula. For example, the stopper may be geometrically attached (ie projection and notch) to the inside of a threaded female luer lock cover. As the coupler is threaded onto the proximal end of the cannula handle it causes compression of the lumenal surface of the stopper around the catheter which fixes the catheter to prevent proximal\distal telescoping within the cannula lumen.

Compression of the lumenal surface of a compressible stopper against the outer catheter surface also creates a "seal" between the stopper and the catheter which prevents leakage of fluid flowing proximal in the cannula from the distal tip. As describe below, the invention also provides another mechanism for prevention of leakage of fluid at the proximal end of the assembly.

In general it is expected that if proximal leakage occurs it is due to proximal flow of fluid, which may be present in or around the distal end of the assembly, up the cannula, around the catheter.

In another embodiment of the invention, proximal fluid leakage is prevented by use of a cannula handle which has a hollowed proximal end comprising a female receptacle. Leakage is prevented by insertion of a "cap" into the receptacle. Generally, a "cap" is a structure which is slidably moveable over the catheter and is interposed between the proximal end of the cannula handle and the distal end of the catheter handle. The cap may have a distal protrusion (male end) whose outside dimension fits within the inside dimension of the female receptacle of the cannula handle. Moving the cap distally causes the distal protrusion of the cap to slide into the female receptacle of the cannula handle. Compression of the cap against the female receptacle of the handle creates a seal which prevents leakage of fluid which may be moving proximally in the cannula. In a preferred embodiment, the cap is within a coupler which is threaded or has some other mechanism for snugly compressing the cap against the proximal end of the cannula handle. It is noted that the male end may be on the proximal cannula handle and the female end on the cap.

In a particularly preferred embodiment, the cap and a slidable stopper (as described above) are a single unit within, for example a threaded coupler. According to this embodiment, the coupler may be threaded on o the proximal end of the handle of the cannula. Threading of the coupler onto the handle causes the distal protrusion of the cap to form a seal within the proximal receptacle of the cannula handle. At the same time, threading the coupler onto the proximal cannula handle compresses the lumenal surface of the stopper around the outer surface of the catheter, thus preventing telescoping of the catheter within the cannula.

The various features and embodiments of the invention will be further described by reference to the figures.

FIG. 1 is a view of one embodiment of a deflectable needle assembly of the invention as it may appear in position for dispensing or removing a medical fluid or surgical instrument. The distal end (1) of the assembly includes the distal tip (2) of the cannula (10), the distal tip (3) of the catheter (12), and the curved distal end (4) of the catheter. The proximal end (5) of the deflectable needle assembly includes the cannula handle (6), the catheter handle (7), and the stylet handle (8). It is noted that the proximal end of the catheter (9) goes through the cannula handle (6). The distal tip of the cannula has a beveled edge (11).

Figure 2:
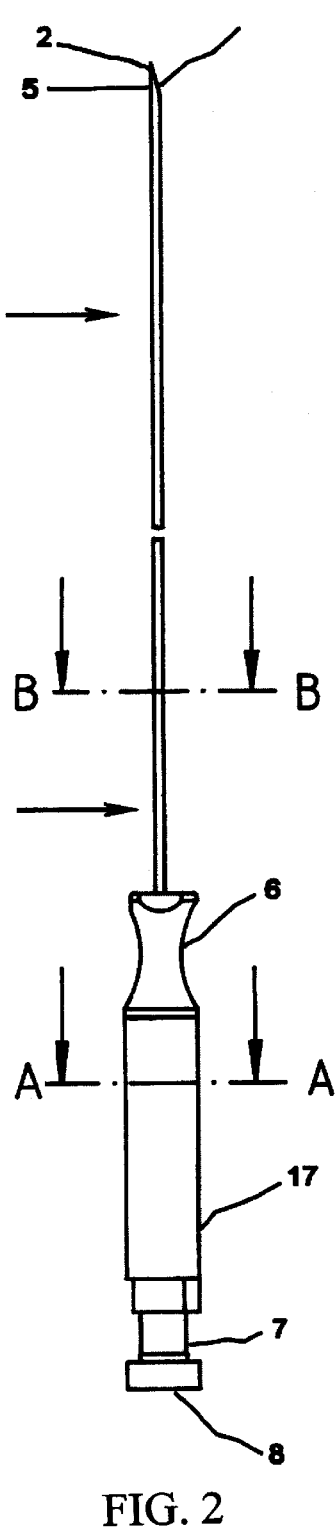
FIG. 2 is a view of the embodiment of a deflectable needle assembly of FIG. 1 arranged for penetration into a penetrable physiological barrier by proximal retraction of the catheter within the lumen of the cannula.
Figure 3:
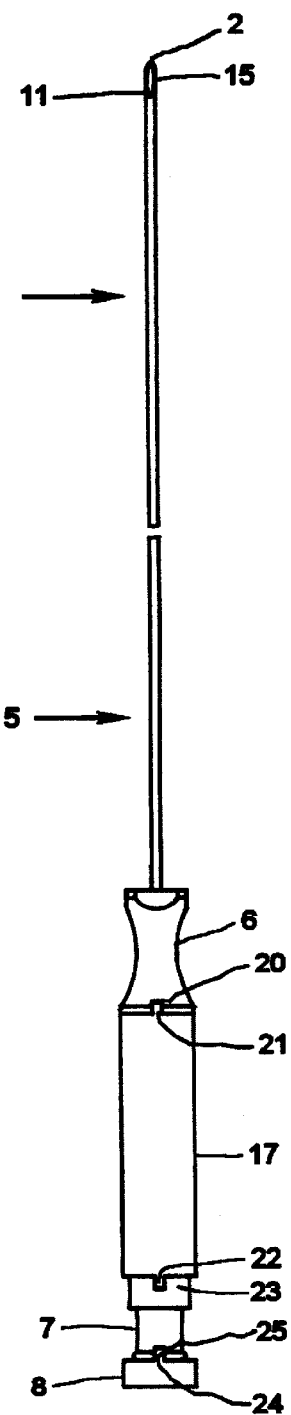
FIG. 3 is a view of the embodiment of a deflectable needle assembly of FIG. 1, rotated 90° with the beveled edge of the distal tip of the cannula facing the viewer.

FIGS. 2 and 3 are views of the embodiment of a deflectable needle assembly of FIG. 1 with the catheter and stylet retracted proximally for penetration of a penetrable physiological barrier. FIG. 3 is rotated 90° from FIG. 2. The distal tip of the assembly (15), in this view, shows the beveled edge (11) of the cannula. The distal tip of the catheter and stylet are retracted distally within the lumen of the cannula and, hence, cannot be seen.

Still referring to FIGS. 2 and 3, the proximal end (5) of this embodiment includes a cannula handle (6), removable stopper insert (17), catheter handle (7) and stylet handle (8). Referring to FIGS. 1–3, it is noted that the length of the removable stopper insert (17) is that which causes the distal tip of the catheter (3) to be within the distal tip of the cannula (2).

Referring to the embodiment in FIG. 3, the proximal end (5) of the assembly shows a handle system wherein the distal end of the cannula handle (6) has a geometrical attachment comprising a projection receiving notch (20) for receiving a projection (21) of the distal end of the removable stopper insert (17). Similarly, the proximal end of the removable stopper insert (17) has a projection (22) which inserts into a notch (23) of the catheter handle (7). In addition, the stylet handle (8) has a projection (24) which inserts into notch (25) at the proximal end of the catheter handle (7). Together, these geometrical attachments provide for the deflectable needle assembly to be fixed as a single unit.

Figure 4:
FIG. 4 is a cross-sectional view of a deflectable needle assembly of FIG. 1 taken at line B—B of FIGS. 2 and 3.

FIG. 4 is a cross-sectional view of a deflectable needle assembly of FIGS. 1–3 taken through line B—B of FIGS. 2 and 3. The stylet (18) is seen within the lumen of the elastic catheter (12) which is within the lumen of the external cannula (10).

Figure 5:
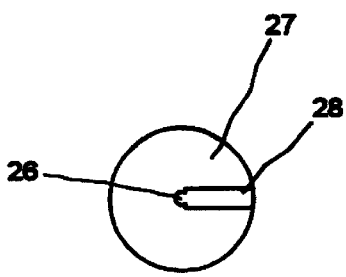
FIG. 5 is a cross-sectional view of the deflectable needle assembly of FIGS. 2 and 3 taken at line A—A.

FIG. 5 is a cross-sectional view of the deflectable needle assembly of FIGS. 1–3, taken through line A—A of FIGS. 2 and 3. This view is through the removable stopper insert of the assembly. It can be seen that the lumen (26) of the removable stopper insert (27) opens to the exterior via a lateral slot (28).

Figure 6:
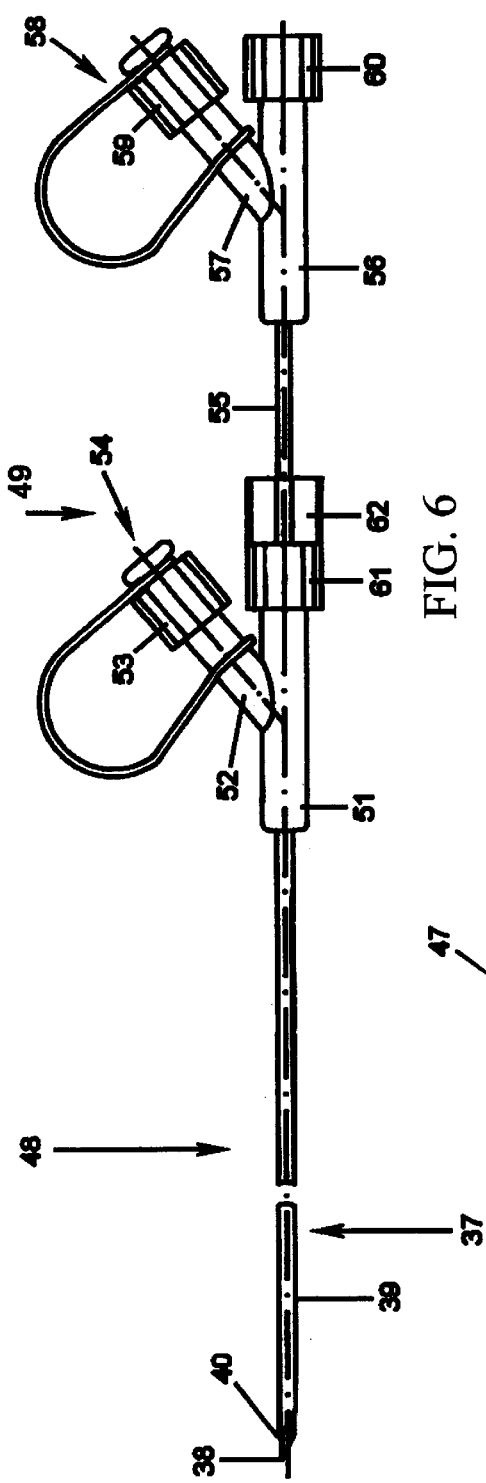
FIG. 6 shows a preferred embodiment of a deflectable needle assembly of the invention with the curved distal end of the catheter retracted proximally.
Figure 7:
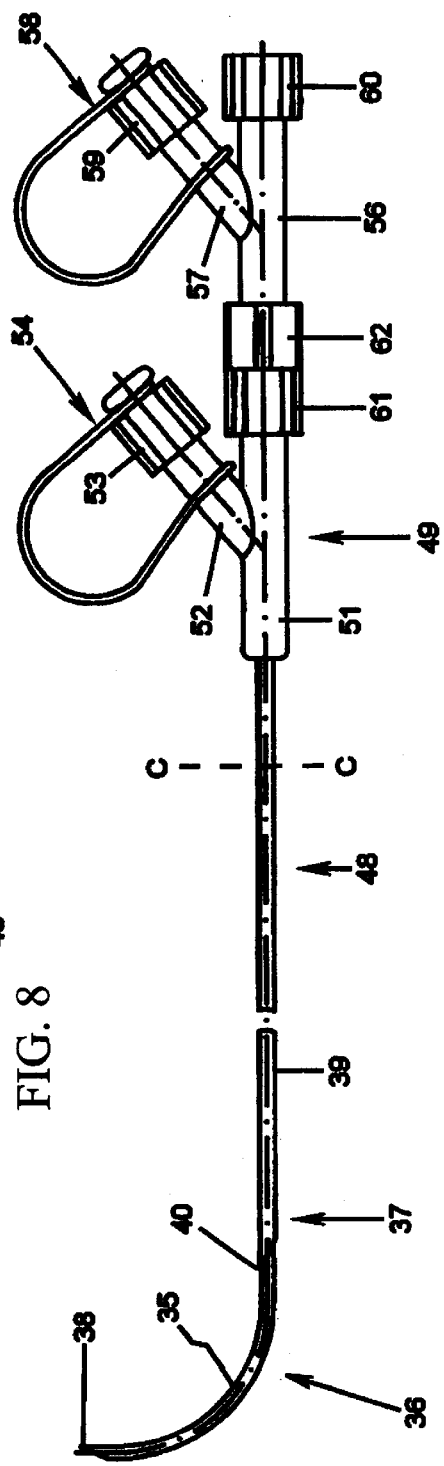
FIG. 7 shows the same preferred assembly of FIG. 6 however, the catheter is protracted distally in the cannula.

FIGS. 6 and 7 show a preferred embodiment of a proximal handle system of a deflectable needle assembly of the invention. FIG. 6 shows the same assembly as in FIG. 7, however, in FIG. 6 the catheter is retracted proximally into the lumen of the cannula (39). Note that in this figure, the catheter is not retracted so far as to create a single beveled edge at the distal end (48). Rather, the distal tip of the catheter (38) and the beveled edge of the distal cannula tip (40) are distinguishable.

FIG. 7 shows the curved end (35) of a distal catheter end (36) with the catheter fully protracted distally from the distal end (37) of the cannula (39). In the drawing, the distal end of the catheter (36) shows a sharp distal tip (38), however, a catheter of the invention need not have a sharp edge.

Figure 8:
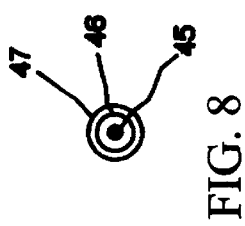
FIG. 8 is a cross-sectional view of the deflectable needle assembly of FIG. 7, taken at line C—C of FIG. 7.

FIG. 8 is a cross-sectional view taken at line C—C of FIG. 7. The cross-sectional view shows the stylet (45) within the lumen of the catheter (46) within the lumen of the external cannula (47).

Referring to the proximal end (49) of the assemblies of FIGS. 6 and 7, the proximal handle will be described. The cannula handle (51) may include an egress\ingress channel (52). The proximal end of the egress\ingress channel (54) may include standard mechanisms for attaching syringes or fluid lines, for example as shown here a cap (53) on a luer lock end (not visible in this view).

FIG. 6 shows a view of the proximal catheter (55) when the distal end of the catheter (36) is retracted within the lumen of the cannula (39). The catheter handle (56) may also include an egress\ingress channel (57) which has a standard opening for attachment of a fluid line or syringe at the proximal end (58), shown here with a cover (59) over a luer lock end (not visible in this view). (60) is the stylet handle. The stylet can be removed by retracting the handle (60) proximally. The proximal aspect of the catheter handle which is covered here by the stylet handle (60), may include a channel opening for attaching a fluid line or syringe as described above.

Figure 9:
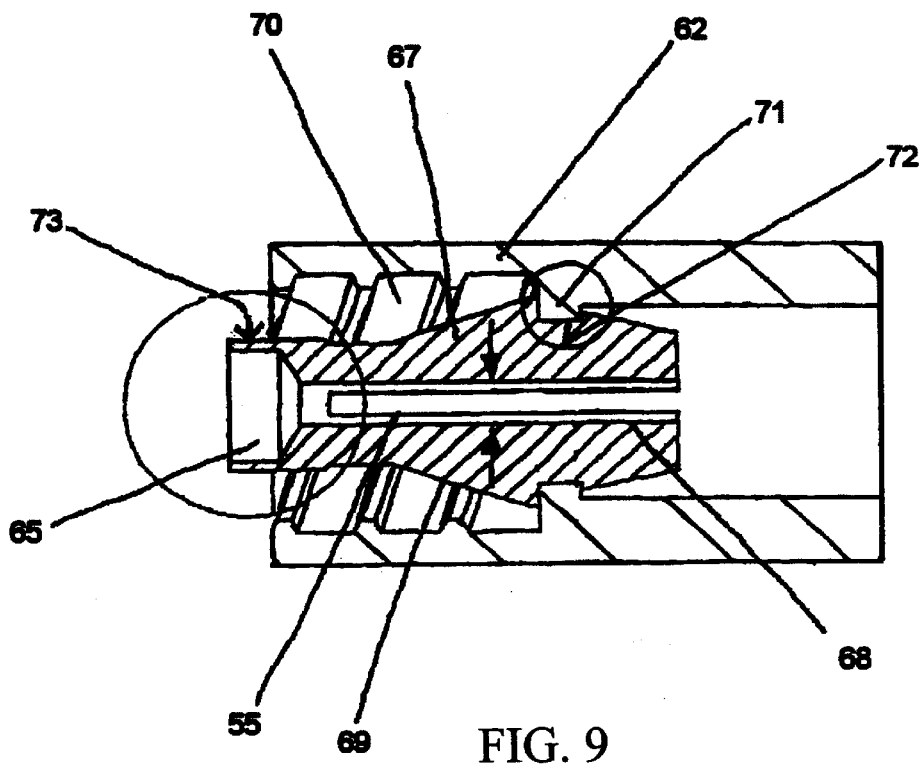
FIG. 9 is a longitudinal cross section of a slidable stopper and cap assembly of the proximal end of a deflectable needle assembly of the invention.
Figure 10:
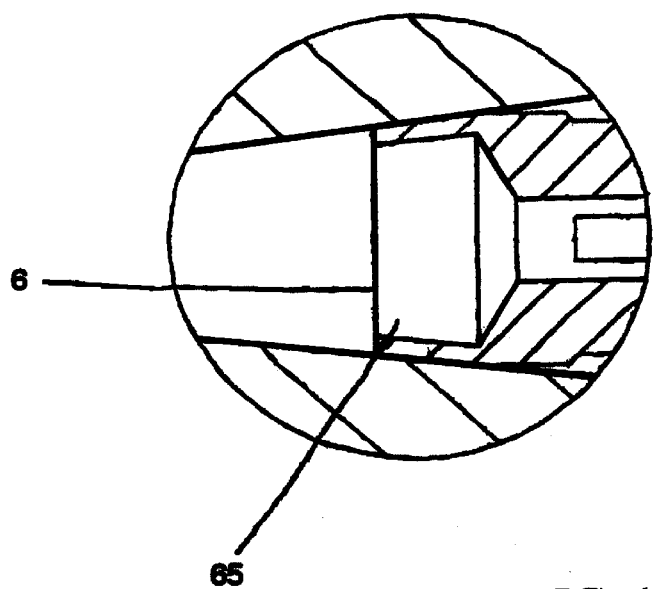
FIG. 10 is a close-up longitudinal cross section of a cap for preventing leakage of fluid at the proximal end of a deflectable needle assembly.

The assembly depicted in FIGS. 6 and 7 also provides for the prevention of proximal or distal sliding of the catheter within the cannula. According to this embodiment, a coupler (62) is present between the cannula handle (51) and the catheter handle (56). A slidable stopper is not visible in FIGS. 6 and 7 because it is covered by the coupler (62). A longitudinal cross-sectional view of the slidable stopper (67), within the coupler, is shown in FIG. 9. FIG. 10 is a close up of the area circled in FIG. 9. The slidable stopper (67) of FIG. 9 is a structure which is slidably movable over the proximal catheter (55) and interposed between the proximal end of the cannula handle and the distal end of the catheter handle (not shown). Still referring to FIGS. 6, 7 and 9, the stopper (67) has a lumenal surface (68) and a peripheral surface (69). The threads (70) of the coupler (62) allow for threading the coupler onto the proximal end of the cannula handle (51). In so doing, the lumenal surface (68) of the stopper (67) is compressed around the proximal catheter (55). Typically, the stopper (67) can be geometrically attached within the coupler (62) using, for example, a projection (71) and projection receiving notch (72). The compression of the lumenal surface (68) of the stopper (67) around the proximal catheter (55) serves two functions. First, it fixes the components of the deflectable needle system as a single unit. Second, it prevents leakage of fluid moving proximally within the cannula.

Another mechanism for preventing proximal fluid leakage is also shown in FIGS. 6, 7, 9 and 10. In FIGS. 6 and 7, the cannula handle (51) contains a hollow proximal end comprising a female receptacle (61). The hollowed receptacle (61), at the proximal end of the cannula, can couple to a coupler (62) which is between the catheter handle and cannula handle (51) as shown. Leakage is prevented by use of a cap. Referring to FIGS. 9 and 10, a cap (65) is seen compressed against an inside surface (66) of the hollowed receptacle (61) of the proximal end of the cannula handle (51) to inhibit leakage of fluid which may be travelling proximally in the cannula system. The exterior surface of the receptacle may have threads (70) for coupling to the coupler (62).

FIGS. 9 and 10 also depict a particularly preferred embodiment. According to this embodiment, the proximal end of the stopper (73) includes a cap (65) which fits within the hollowed inside surface (66) the receptacle (61) of the proximal end of the cannula handle (51). Thus, use of this embodiment provides for prevention of fluid leakage and fixation of the telescoping components when the coupler (62) is coupled to the proximal end of the cannula handle (51).

All patents in the specification are indicative of the level of ordinary skill in the art to which this invention pertains and are incorporated herein by reference.

It will be apparent to one of ordinary skill in the art that many changes and modifications can be made in the invention without departing from the spirit or scope of the appended claims.

I claim:

1. A deflectable needle assembly for accessing a physiological site in a body, wherein said access to said physiological site is obstructed by a non-penetrable object, said deflectable needle assembly comprising a proximal end and a distal end and:

a cannula, said cannula having a lumen, a proximal end, a distal end and a beveled distal tip;

a catheter, said catheter having a lumen, a proximal end, a curved distal end, and a beveled distal tip, wherein said catheter can be inserted within said lumen of said cannula such that said distal end and said distal tip of said catheter can be protracted distally beyond, or retracted proximally within, said distal end of said lumen of said cannula and said catheter can be axially rotated within said lumen of said cannula; and a stylet, said stylet having a proximal end and a distal end and said stylet can be inserted in said lumen of said catheter, wherein said curved distal end of said catheter is straight when said catheter is retracted proximally within said distal end of said lumen of said cannula.

2. The deflectable needle assembly according to claim 1 comprising more than one catheter.

3. The deflectable needle assembly according to claim 1 wherein said catheter is manufactured from a selected one of an elastic and superelastic material.

4. The deflectable needle assembly, according to claim 1 wherein said catheter is comprised of nickel titanium (NiTi).

5. The deflectable needle assembly according to claim 1 wherein said distal tip of said catheter has a sharp edge.

6. The deflectable needle assembly according to claim 1 wherein at least one of said cannula, catheter and stylet is comprised of a material which avoids causing an artifact on a diagnostic image.

7. The deflectable needle assembly according to claim 1 wherein said proximal end of said deflectable needle assembly further comprises a handle attached to said proximal end of at least one of said cannula, said catheter, and said stylet for operating said deflectable needle assembly.

8. The deflectable needle assembly according to claim 7 wherein at least one of said cannula handle, said catheter handle, and said stylet handle further comprises an egress/ingress channel.

9. The deflectable needle assembly according to claim 1 wherein said proximal end of said deflectable needle assembly further comprises:
   a cannula handle;
   a catheter handle; and
   a stopper
   wherein said stopper is interposable between said cannula handle and said catheter handle and said stopper prevents retraction or protraction of said catheter within said lumen of said cannula.

10. The deflectable needle assembly according to claim 9 wherein said stopper is a removable insert.

11. The deflectable needle assembly according to claim 9 wherein said stopper is slidably movable along said catheter; said stopper having a lumenal surface and said stopper is attached to a coupler which can couple to said cannula handle such that when said coupler is coupled to said cannula handle said lumenal surface of said stopper is compressed around said catheter.

12. The deflectable needle assembly according to claim 11 wherein compression of said stopper around said catheter prevents fluid leakage at said proximal end of said deflectable needle assembly.

13. The deflectable needle system according to claim 11 wherein said coupler threads onto said cannula handle.

14. The deflectable needle assembly according to claim 1 wherein said proximal end of said deflectable needle assembly further provides for prevention of fluid leakage at said proximal end of said cannula; said deflectable needle assembly comprising:
   a cannula handle, said cannula handle having
      a proximal hollowed female receptacle; and
   a cap
   wherein said cap inserts within said proximal hollowed female receptacle of said cannula handle.

15. The deflectable needle assembly according to claim 1 wherein said proximal end of said deflectable needle assembly further comprises a stopper to prevent retraction or protraction of said catheter within said lumen of said cannula and a cap to prevent leakage of fluid at said proximal end of said needle assembly.

16. The deflectable needle assembly according to claim 15 wherein said stopper and said cap comprise a single unit.

* * * * *

UNITED STATES PATENT AND TRADEMARK OFFICE
CERTIFICATE OF CORRECTION

PATENT NO. : 6,572,593 B1 Page 1 of 1
DATED : June 3, 2003
INVENTOR(S) : Wolfgang Rudolf Daum It is certified that error appears in the above-identified patent and that said Letters Patent is hereby corrected as shown below:

<u>Column 8,</u>
Line 17, "threaded on o the proximal" should read -- threaded onto the proximal --.

Signed and Sealed this

Eighteenth Day of November, 2003

JAMES E. ROGAN
*Director of the United States Patent and Trademark Office*